United States Patent [19]

Amini

[11] Patent Number: 4,910,688
[45] Date of Patent: Mar. 20, 1990

[54] ON-MACHINE SHEET MATERIAL PROPERTY ANALYSIS

[75] Inventor: Junis Amini, Vaudreuil, Canada

[73] Assignee: Domtar Inc., Montreal, Canada

[21] Appl. No.: 177,488

[22] Filed: Apr. 1, 1988

[51] Int. Cl.⁴ ..................... G06F 15/46; G01G 11/04
[52] U.S. Cl. ............................... 364/551.01; 364/471; 364/568
[58] Field of Search ............... 364/469, 471, 473, 485, 364/550, 551.01, 568, 724.06, 724.07, 726

[56] References Cited

U.S. PATENT DOCUMENTS

| | | | |
|---|---|---|---|
| 3,610,899 | 10/1971 | Dahlin | 364/571 |
| 3,612,839 | 11/1971 | De Witt | 364/568 |
| 3,936,665 | 2/1976 | Donoghue | 364/568 |
| 4,400,089 | 8/1983 | Farabaugh | 364/473 |
| 4,453,404 | 6/1984 | Powell et al. | 364/471 |
| 4,720,808 | 1/1988 | Repsch | 364/568 |

OTHER PUBLICATIONS

Pillo et al.: On the Analogue Methods for Power Spectral Density Estimation, International Journal of Control, vol. 11, No. 5, 1970, pp. 759-770.

Murthy et al.: a Practical Cross-Power Spectral Analyzer, Simulation, vol. 32, Jan. 1978, pp. 9-15.

*Primary Examiner*—Felix D. Gruber
*Attorney, Agent, or Firm*—Antoine H. Gauvin

[57] ABSTRACT

A method and apparatus for determining on-machine, components of variances over an entire frequency range, of a property of a substantially continuous moving sheet material. At least two property-sensing detectors measure and each provide a signal Y(t) proportional to a sheet material property at a different location in the cross machine direction of a moving sheet material. Preferably a spectrum analyzer, determines the power spectral density function G(f) for each detector's signal, and the coherence function COH(f) between the two detectors' signals. On the basis of these results, the total variance, the machine direction variance, the residual variance and the contributions of the machine-directional cyclic and non-cyclic variances of the property of interest are determined, preferably by a computer. These contributions are generally indicative of process and/or machine upsets.

18 Claims, 5 Drawing Sheets

ON-MACHINE SHEET MATERIAL PROPERTY ANALYSIS

FIELD OF THE INVENTION

This invention relates to a method and an apparatus for determining on-machine, components of variances over an entire frequency range, of a property of a substantially continuous moving sheet material and more particularly to a method and apparatus for determining on-machine, total, machine direction, machine-directional cyclic, machine-directional non-cylic, and residual variances of a property of a moving sheet material.

BACKGROUND OF THE INVENTION

Various materials are manufactured in the form of a substantially continuous sheet material. For example, a web of sheet paper is manufactured by continuously depositing an aqueous suspension of fibers onto a traveling wire. Much water is drained from the wet sheet through the wire. The wet sheet is further dewatered by a press section, dried by driers and finished and smoothed by calendars. The sheet of paper produced is substantially continuous and relatively wide, generally 10 to 20 feet.

It is generally desirable to maintain certain properties of the sheet material substantially constant in the direction of the traveling sheet (machine direction or MD) and perpendicular thereto (cross machine direction or CD). However, during the manufacture of sheet material, numerous possible process and/or machine upsets may occur and it is most difficult to determine their sources. When pure machine direction variance over an entire frequency range is detected for a property of interest and decomposed into its cyclic and non-cyclic components, the sources of these components are more easily determined and corrected. However, a random variance is superposed on the pure machine direction variance, therefore the latter can not be clearly distinguished by a single detector.

Methods have been described wherein a property is obtained at a plurality of points by one or two sensors moving perpendicularly across the sheet material. Such method is taught in U.S. Pat. No.. 3,610,899 as invented by E. Dahlin and issued on Oct. 5, 1971. The data is recorded and manipulated to obtain MD and CD profiles or variances in their time domain of the property of interest and then control for example, the slice adjustment of the paper machine, accordingly. However, since the sheet material is moving in the machine direction while the sensors move across the sheet, the plurality of points are diagonally taken on the sheet. Thus, points taken on a same machine-directional line are far apart, i.e. 60 feet, and cannot detect fluctuations shorter than 120 feet (as per Nyquist Theorem). The profiles and variances are obtained after exponential weighing or filtering of the data in the time domain, which is non-indicative of the frequency composition of these variances. Also, filtering results in the loss of the contributions at higher frequencies. Furthermore, Dahlin does not distinguish between cyclic and non-cyclic MD variances.

It is an object of the present invention to provide a method and apparatus for determining on-machine, components of variances over an entire frequency range, of a property of a substantially continuous moving sheet material.

It is also an object of this invention to determine on-machine, total, machine direction, machine-directional cyclic and non-cyclic, and residual variances of a property of a moving sheet material.

It is a further object of this invention to determine residual variances at a plurality of zones across a moving sheet material.

BRIEF DESCRIPTION OF THE INVENTION

Broadly stated, the invention is directed to a method for automatically determining on-machine, components of variances over an entire frequency range (f), of a property of a substantially continuous sheet material comprising:

(a) allowing said substantially continuous sheet material to ravel in a machine direction (MD), (b) scanning said property from at least two locations in a zone across said sheet material and automatically providing an output signal proportional to said property at each of said locations, (c) transforming at least two of said output signals into their corresponding power spectral density functions, (d) from a pair of said power spectral density functions, determining a coherence function, (e) from said coherence function, computing a square root function of said coherence function, (f) multiplying said square root function by a first power spectral density function of said pair in step d), thereby obtaining a machine direction output power, MDOP(f), (g) from said machine direction output power, MDOP(f), determining a machine direction variance over said entire frequency range, $V_{MD}$, by $$V_{MD} = \sum_{i=1}^{n} MDOP(f_i)$$

where $MDOP(f_i)$ is the machine direction output power at a frequency $f_i$, and n is the number of frequencies in said entire frequency range.

The invention is also directed to an apparatus for automatically determining on-machine, components of variances over an entire frequency range f, of a property of a substantially continuous sheet material moving in machine direction (MD), comprising:

(a) at least two detectors, each for scanning said property in said machine direction and at a different location in a zone across said moving sheet material, (b) at least two of said detectors each providing a detector output signal proportional to said property, (c) means for detecting and transforming at least two of said detector output signals into their corresponding power spectral density functions, (d) responsive to said means for detecting and transforming, a means for determining a coherence function corresponding to a pair of said power spectral density functions, (e) responsive to said means for determining a coherence function, a means for determining a square root function of said coherence function, (f) responsive to said means for determining a square root function, a means for multiplying said square root function by a first power spectral density function of said pair, thereby obtaining a machine direction output power, MDOP(f), (g) responsive to said means for multiplying, a means for determining a machine direction variance over said entire frequency range, $V_{MD}$, by $$V_{TOT,2} = \sum_{i=1}^{n} TOTOP_2(f_i)$$

where $MDOP(f_i)$ is the machine direction output power at a frequency $f_i$, and n is the number of frequencies in said entire frequency range.

BRIEF DESCRIPTION OF THE DRAWINGS

Referring now to the drawings which illustrate the invention.

Figure 1:
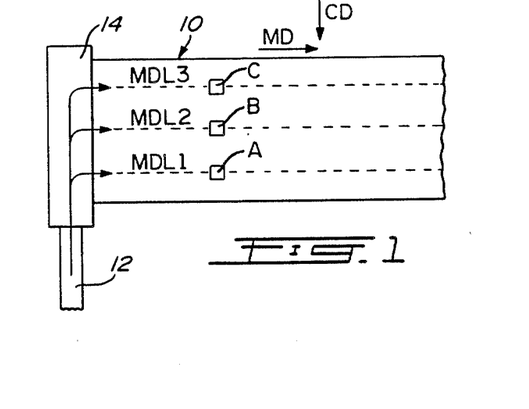
FIG. 1 is a plan view of a typical sheet material manufacture.

Referring now to FIG. 1, there is shown an overhead view of a typical means for producing substantially continuous sheet material 10. Fluid for producing sheet material flow through conduit 12, into flow spreader 14 and usually onto a moving wire (not shown). The fluid spread onto the wire forms sheet material 10 which is traveling in the MD or machine direction. Perpendicular to the MD direction and in the plane of sheet material 10 is the CD or cross-machine direction.

Assuming, for example and not as a limitation, that the fluid flow in conduit 1 is unsteady. The fluctuations in the flow will first cause fluctuations in the properties of the sheet material at MDL1 (machine direction line 1), then at DDL2 and finally at MDL3. Two or more property-sensing detectors A, B and C for eample, are mounted above and/or below the machine direction lines MDL1, example and MDL3 respectively and measure a sheet material property of interest with respect to time (time history record). The detectors are preferably mounted side by side in a cross-machine direction either on a stationary frame or a removable frame, not shown. However, the detectors may not be mounted side by side, as long as none are aligned in the machine direction. Ideally, the detectors A, B and C will each provide a detector output signal proportional to the property of interest, each output signal having the same fluctuations in that property. However, the detector output signals will contain residual fluctuations (noise), and will be out of phase from each other, thereby hiding the similarities between the detector output signals.

Figure 2:
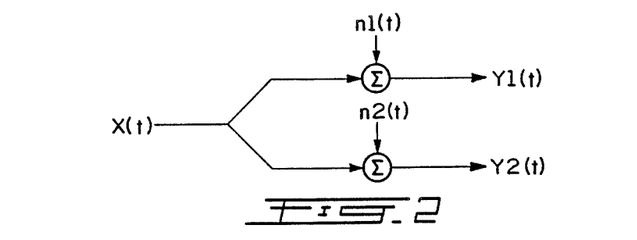
FIG. 2 is a diagram showing the relation between input, output and noise signals.

There is shown in FIG. 2, a diagram demonstrating how the above described fluctuations and signals can be interpreted. For way of example only, the following will consider only two detector output signals. X(t), considered as the input signal is the time history record of the property fluctuations common at all machine direction lines on a travelling sheet material. To this common X(t) signal is added, at each machine direction line, MDL1 and MDL2, extraneous noise n1(t) and n2(t) respectively (for example, due to turbulence in the jet exiting the headbox or in the forming area of a paper machine), the results being detected at each machine direction line, yy detectors A and B as detector output signals Y1(t) and Y2(t). There is a linear relationship between the signals Y1 and Y2 which can be extracted through spectral density functions, thereby transforming the time history records into their frequency domains.

The time histories Y1(t) and Y2(t) are transformed into their power spectral density functions $G_{11}(f)$ and $G_{22}(f)$ respectively, frequency f always representing all frequencies $f_1, f_2, f_3 \ldots f_n$. Their power cross-spectrum $G_{12}(f)$ is also computed. The mathematical techniques of obtaining power spectral density functions by Fourier transforms or analog filtering, appear in various texts, such as "Random Data: Analysis an Measurement Procedures" by J. S.. Bendat and A. G. Piersol, Wiley—Interscience, 1971.

Power spectral density function $G_{22}(f)$ is equivalent to total output power at frequency f, at position 2, $TOTOP_2(f)$. "Position 2" represents that this result is based upon detector output signal Y2(t). Accordingly, power spectral density function $G_{11}(f)$ is equivalent to total output power at frequency f, at position 1, $TOTOP_1(f)$, as this result is based upon detector output signal Y1(t). For sake of consistency, "position 2" will be used throughout the following discussion. Total output power at frequency f, $TOTOP_2(f)$, summed over frequencies $f_1, f_2 \ldots f_n$ is equivalent to total variance at position 2, $V_{TOT,2}$ (and similarly for $V_{TOT,1}$) where:

$$V_{TOT,2} = \sum_{i=1}^{n} TOTOP_2(f_i)$$

The degree to which signal Y2 depends on signal Y1 is expressed by the coherence function $COH_{12}(f)$ where:

$$COH_{12}(f) = \frac{|G_{12}(f)|^2}{G_{11}(f) \cdot G_{22}(f)} \leq 1$$

When $COH_{12}(f) = 0$ at a particular frequency, Y1(t) and Y2(t) are incoherent or uncorrelated at that frequency. If $COH_{12}(f) = 1$ for all frequencies, Y1(t) and Y2(t) are said to be fully coherent.

In FIG. 2, the detector output signals Y1(t) and Y2(t) are out of phase and contain similar extraneous noise n1(t) and n2(t) respectively, which are uncorrelated and incoherent with each other and with noiseless signal X(t). The extraneous noise n1(t) and n2(t), being similar, are considered substantially equal. Their power spectral density functions $G_{n1n1}(f)$ and $G_{n2n2}(f)$ respectively, are also substantially equal. $G_{n2n2}(f)$ and $G_{n1n1}(f)$, are equivalent to residual output power at frequency f, at position 2, $RESOP_2(f)$, and residual output power at frequency f, at position 1, $RESOP_1(f)$, respectively. Residual output power at frequency f, $RESOP_2(f)$, summed over frequencies $f_1, f_2 \ldots f_n$ is equated to residual variance at position 2, $V_{RES,2}$ (and similarly for $V_{RES,1}$) where:

$$V_{RES,2} = \sum_{i=1}^{n} RESOP_2(f_i)$$

$G_{XX}(f)$, the power spectral density function of $X(t)$ is equivalent to the pure machine direction output power at frequency f, at position 2, $MDOP_2(f)$ and is obtained by $$G_{XX}(f) = MDOP_2(f) = \sqrt{COH_{12}(f)} \cdot TOTOP_2(f)$$
$$= \sqrt{COH_{12}(f)} \cdot G_{22}(f)$$

$COH_{12}(f)$ and $G_{22}(f)$, (or $TOTOP_2(f)$), being known, (having previously been computed), $G_{XX}(f)$, equivalent to $MDOP_2(f)$, is determined. Machine direction output power at frequency f, $MDOP_2(f)$ summed over frequencies $f_1, f_2 \ldots f_n$ is equated to machine direction variance at position 2, $V_{MD,2}$ where:

$$V_{MD,2} = \sum_{i=1}^{n} MDOP_2(f_i)$$

Thus, $V_{RES,2}$ is equal to the difference between the total variance and the pure machine direction variance. If the $RESOP_2(f)$ is desired, it is obtained by $RESOP_2(f)==TOTOP_2(f)-MDOP_2(f)$.

Figure 10:
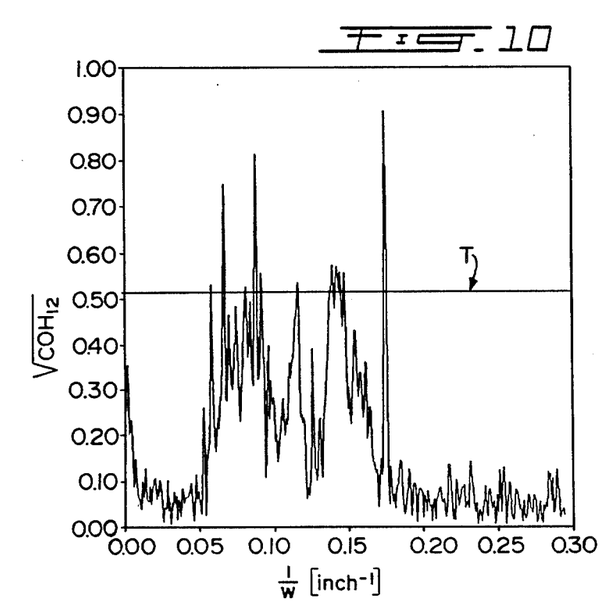
FIG. 10 is a graph showing the square root of coherence function, $\sqrt{COH_{12}}$ versus inverse wavelength 1/w, and also showing threshold value T.

When a graph is made of the square root of the coherence function, $\sqrt{COH_{12}(f)}$, (or of the coherence function itself, versus frequency, it is often noticed that $\sqrt{COH_{12}(f)}$, (or $COH_{12}(f)$), peaks at certain frequencies. These are considered to be frequencies at which the common fluctuations in the detector output signals are cyclic machine-directional. Thus, it is considered that the amount of $MDOP_2(f)$ corresponding with each of these peak frequencies, contributes to a cyclic machine-direction output power at frequency f, at position 2, $CMDOP_2(f)$. The sum of $CMDOP_2(f)$ over all frequencies $f_1, f_2 \ldots f_n$ is equal to cyclic machine direction variance, at position 2, $V_{CMD,2}$. The individual peak frequencies $f_p$, are usual indicative of and can be useful in determining the sources of cyclic fluctuations particularly due to machine and/or process upsets. The above mentioned peaks can be visually detected from the graph, however a more practical criterium for peak detection is the following. A threshold value T is computed as $$T = m + 1.96s$$

where m is the mean value of the function $\sqrt{COH_{12}(f)}$ over all the frequencies analyzed and s is its standard deviation. The factor 1.96 is arbitrary but was chosen from experience and it corresponds to a 97.5% confidence level for a one-sided significance test on a Gaussian Distribution. The factor 1.96 may be altered to preferably remain in the range of 1 to 3.29 corresponding t a range of 84% to 99.95% confidence level respectively.

At each frequency, the value $\sqrt{COH_{12}(f)}$ is compared to T and when $\sqrt{COH_{12}(f)}$ is greater than or equal to T, the value of $MDOP_2(f)$ corresponding with that frequency contributes to $CMDOP_2(f)$. This comparison is repeated at each frequency to obtain the entire $CMDOP_2(f)$, the latter summed at frequencies $f_1, f_2 \ldots f_n$ to obtain $V_{CMD,2}$. Then $V_{CMD,2}$ is subtracted from $V_{MD,2}$ thereby obtaining the non-cyclic machine direction variance at position 2, $V_{NCMD,2}$. If desired, $CMDOP_2(f)$ may be subtracted from $MDOP_2(f)$ to obtain the non-cyclic machine direction output power at frequency f, at position 2, $NCMDOP_2(f)$. The sum of $NCMDOP_2(f)$ at frequencies $f_1, f_2 \ldots f_n$ would also be equal to $V_{NCMD,2}$. In order to demonstrate which variances can be considered more important, and thereby assessed first in order to correct process and/or machine upsets which contributed to them, the following percentages are preferably computed.

1. The percentage of machine direction to total variances $$MD/TOT\ \% = V_{MD,2}/V_{TOT,2} \times 100$$

2. The percentage of residual to total variances $$RES/TOT\ \% = V_{RES,2}/V_{TOT,2} \times 100$$

3. The percentage of cyclic machine direction to total variances $$CMD/TOT\ \% = V_{CMD,2}/V_{TOT,2} \times 100$$

4. The percentage of non-cyclic machine direction to total variances $$CMD/TOT\ \% = V_{NCMD,2}/V_{TOT} \times 100$$

5. The percentage of cyclic machine direction to machine direction variances $$CMD/MD\ \% = V_{CMD,2}/V_{MD,2} \times 100$$

6. The percentage of non-cyclic machine direction to machine direction variances $$NCMD/MD\ \% = V_{NCMD,2}/V_{MD,2} \times 100 = 100 - CMD/MD\ \%$$

Throughout the previous analysis, it was assumed that the residual variance is substantially eual at every location in the cross machine direction, whereby the two detectors may be located at any location in the cross machine direction. However, the property analysis may be done for multiple zones of the moving sheet material and the residual variance for each zone compared with each other. In order to enable multiple zone property analysis, two detectors may be movably mounted with the location of the detectors changed after the property analysis of each zone. Or, more than one detector can be used, their signals analyzed in pairs across the sheet material. This multiple zone comparison may detect significant changes in residual variance across the sheet material caused for example, by local turbulence, particularly near the edges of the sheet material.

Furthermore, the previous analysis is based on the dependency of time history $Y_2(t)$ on time history $Y_1(t)$. However, substantially identical variances TOT, MD, RES, CMD, NCMD) will be obtained when the analysis is based on the dependency of time history $Y_1(t)$ on time history $Y_2(t)$, and/or "position 1".

The methods described above apply for numerous types of sheets or webs and numerous scalar properties of the sheet or web. For example, these methods are applicable to basis weight, moisture and temperature of paper moving on a paper machine; basis weight and moisture of roofing felts; density of roofing shingles; and density of extruded polymer films such as polyethylene.

EXAMPLE

The above described methods have been applied to a paper machine, analyzing its basis weight (weight per unit surface).

Figure 3:
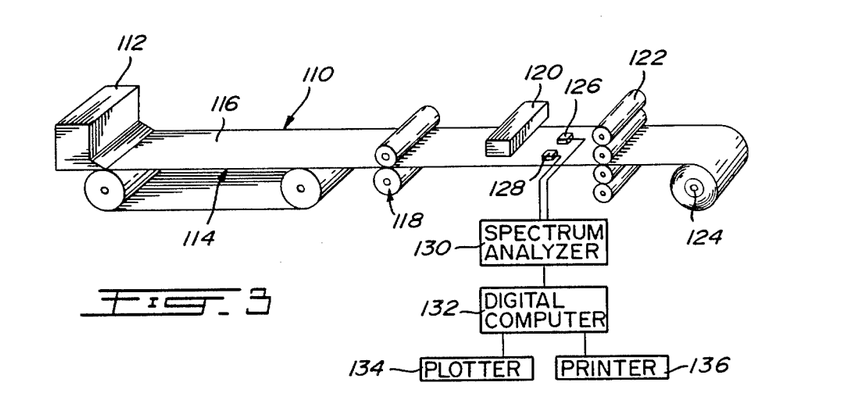
FIG. 3 is a diagram of a paper machine including a preferred embodiment of the present invention.

Referring now to FIG. 3, in paper machine 110, an aqueous suspension of fibers continuously flows from headbox 112 onto web 114, forming sheet of paper 116. Sheet 116 travels through press section 118, is dried by drier section 120 and is finished and smoothed by calendars 122. The finished sheet 116 is wound on roll 124. The above describes only the general appearance of a paper machine as well known by one skilled in the art.

Two basis weight detectors 126 and 128 are mounted preferably said by side above sheet 116 between drier section 120 and calendars 122.

The detectors 126 and 128 ar preferably sensitive and fast such as recent germanium detectors equipped with a cryostat. Other well known basis weight detectors such as light probes may be used mounting them as necessary with respect to the wet end or dry end of paper machine 110 according to the manner the detectors must operate.

Figure 4:
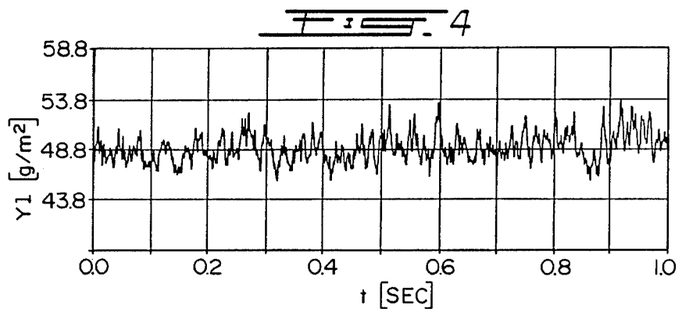
FIG. 4 is a graph showing a tim history record of basis weight, Y1, versus time t.
Figure 5:
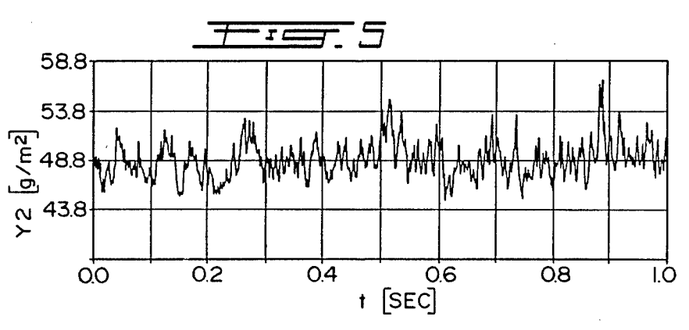
FIG. 5 is a graph showing a time history record of basis weight, Y2, versus time t.
Figure 6:
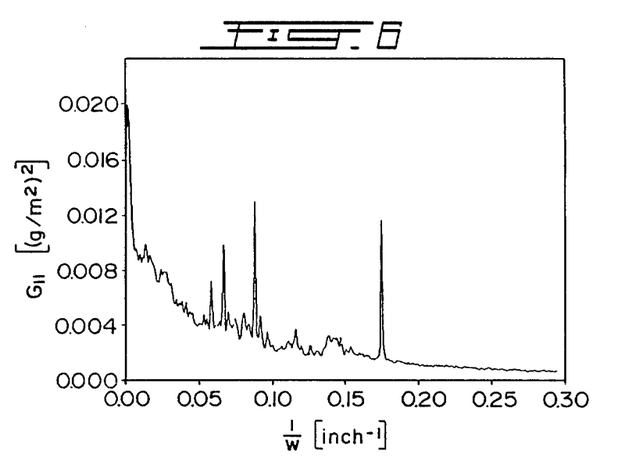
FIG. 6 is a graph sowing power spectral density function $G_{11}$ versus inverse wavelength 1/w.
Figure 7:
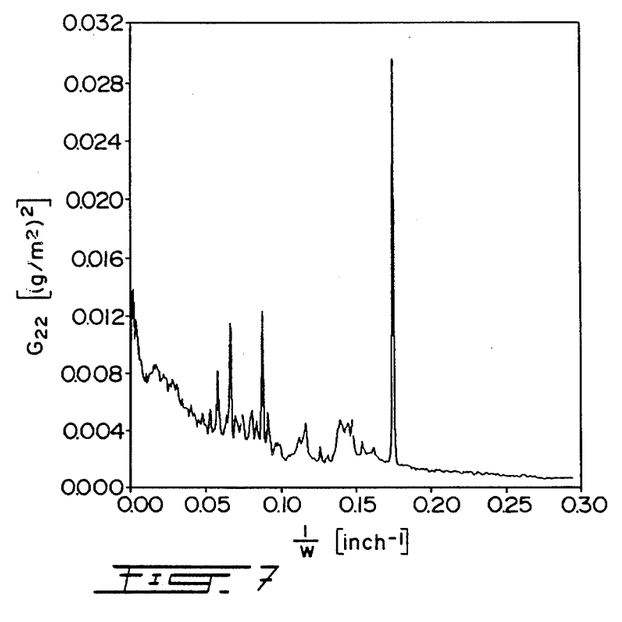
FIG. 7 is a graph showing power spectral density function $G_{22}$ (which is equivalent to total output power TOTOP) versus inverse wavelength 1/w.
Figure 8:
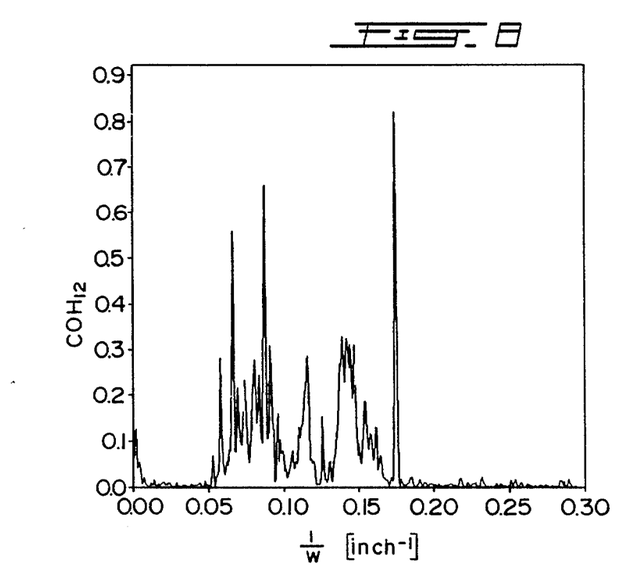
FIG. 8 is a graph showing coherence function $COH_{12}$ versus inverse wavelength 1/w.
Figure 9:
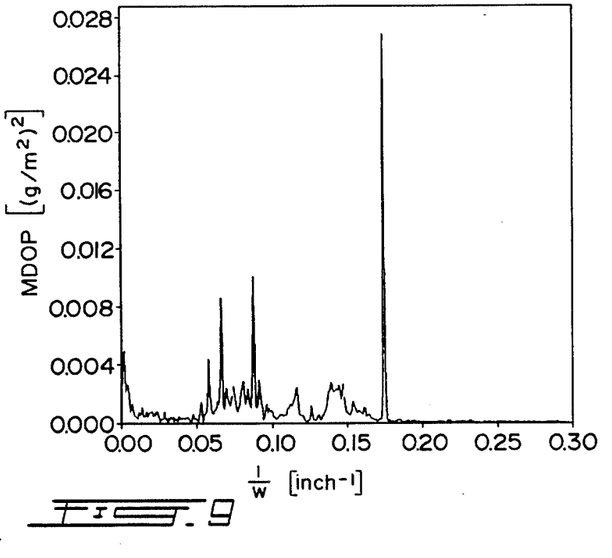
FIG. 9 is a graph showing machine direction output power MDOP versus inverse wavelength 1/w.

The detectors 126 and 128 scan sheet 116 to detect the basis weight of the moving sheet of paper for example at about every 3.91 milliseconds for a period of 20 minutes. Simultaneously, the detectors 126 and 128 develop an analog signal Y1(t) and Y2(t) respectively, which represents the paper's basis weight as it is scanned. Optionally, the analog signals Y1(t) and Y2(t) are converted by a plotter into plots of Y1(t) and Y2(t) with respect to time, as shown in FIGS. 4 and 5 respectively for a shortened period of 1 second.

Figure 11:
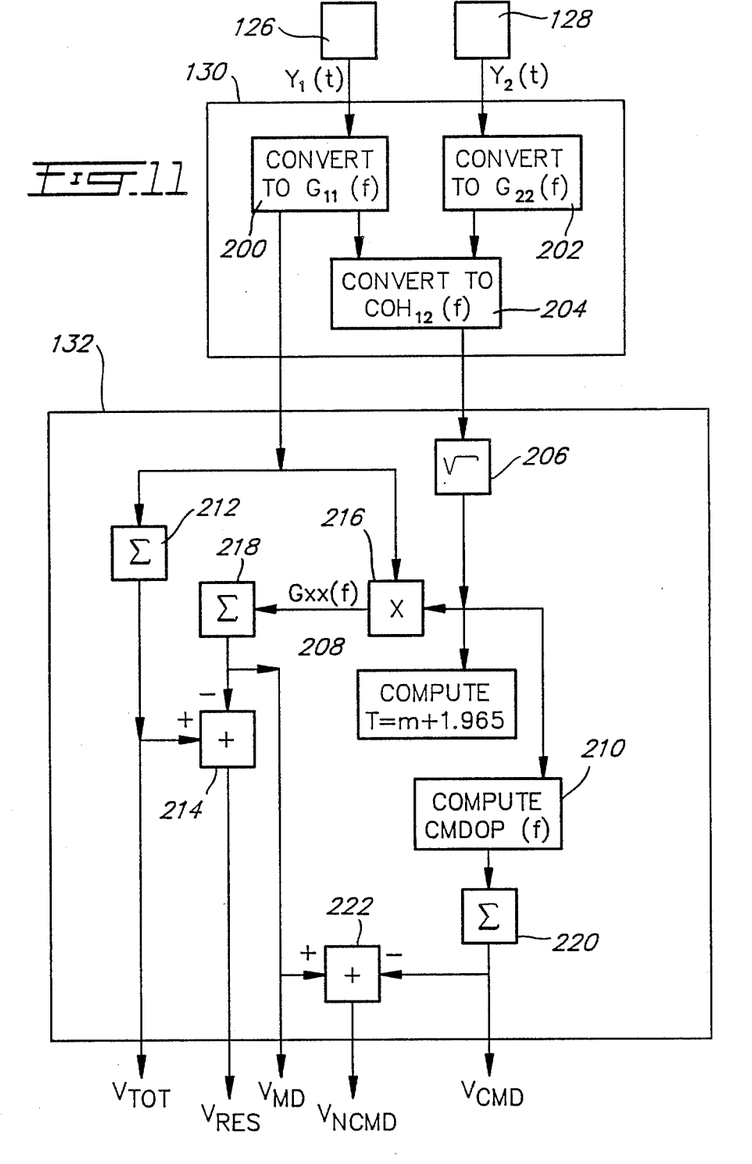
FIG. 11 is a diagram showing the steps performed by some of the elements of FIG. 3 in accordance with an accordance with an embodiment of the invention.

A spectrum analyzer 130 using Fast Fourier Transforms, such as SD-375 by Spectral Dynamics Inc., receives the analog signals Y1(t) and Y2(t and, at four second intervals, converts them at 200 and 202 into their power spectral density functions $G_{11}(f)$ and $G_{22}(f)$ and aso computes at 204 their coherence function $COH_{12}(f)$ over a discrete frequency range. At every four seconds for a period of 20 minutes, new spectra of $G_{11}(f)$, $G_{22}(f)$ and, $COH_{12}(f)$ are computed. The newly computed $G_{11}(f)$, $G_{22}(f)$ and $COH_{12}(f)$ are added to their corresponding averaging memories. After the 20 minute period, ensemble averages are obtained over the 300 spetra. With these averaged spectra, the digital computer 132 computes $\sqrt{COH_{12}(f)}$ at 206, the threshold value T at 208, and CMDOP(f) at 210. Then computer 132 computes $V_{TOT}$ at 212, $V_{RES}$ at 214, $V_{MD}$ via 206, 216, 218, $V_{CMD}$ at 220, $V_{NCMD}$ at 222 and the percentages of $V_{CMD}$ and $V_{NCMD}$ to $V_{MD}$ and $V_{TOT}$. (The "position 2" has been omitted for simplicity).

The computer optionally transfers the averaged $G_{11}(f)$, $G_{22}(f)$, $COH_{12}(f)$, MDOP(f) and $\sqrt{COH_{12}(f)}$ and T to plotter 134 which plots these values versus frequency or versus inverse wavelength 1/w as shown in FIGS. 6 to 10 respectively. The relationship between frequency and wavelength will be described later. Printer 136 prints the frequencies $f_p$ at which there are contributions to the cyclic MD variance (which computer 12 inherently computed) and the various variances and their percentages. With these results, one skilled in the art can determine which type of variances are most prevalent and how to correct them.

The above mentioned preferred averaging of $G_{11}(f)$, $G_{22}(f)$ and $COH_{12}(f)$ may be done according to different methods as one skilled in the art may choose. One method is to compute a linear average as outlined above. Another preferred method is to compute a sliding average of $G_{11}(f)$, $G_{22}(f)$, and $COH_{12}(f)$, whereby with the use of commonly known time weighing or exponential weighing, updated averaged values are available at about every four seconds. Thus, if something upsets the analysis within the 20 minute period, such as a break in the paper web, all the variances may still be computed, using the last available averaged values, to help determine the cause of the upset.

From experience, it has been found that when RES/TOT% is much greater than MD/TOT%, fluctuations originate in the forming zone and headbox of the paper machine. When MD/TOT% is much greater than RES/TOT% fluctuations originate upstream of the headbox, in the approach system. When CMD/MD% is high, the fluctuations originate in pumps, screens, vibrations, etc.

The spectrum analyzer 130, digital compute 132, plotter 134 and printer 136 are preferably portable wherein they can be easily moved, along with the removably mounted detectors 126, 128, from one paper machine to another. Thereby, the complete variance analysis is entirely done on-machine.

The graphs shown in FIGS. 4 to 10 are optional, either being drawn by plotters or displayed on screens, and they were presented here for illustrative purposes. However, the results that one would usually desire are given in Table 1, as printer 136 would supply (and/or an optional screen could display) at 20 minute intervals. In this case, computer 132 performed the additional calculation of transforming the minimum frequency and the maximum frequency of the discrete range of frequencies, including the peak frequencies $f_p$ into their equivalent wavelengths w according to (in the imperial system):

$$w = \frac{(\text{speed of paper})}{5 \times f}$$

where wavelength w is in inches, speed of paper in feet per minute, and frequency f in Hertz. In the case of metric measurements, $$w = \frac{(\text{speed of paper})}{f}$$

where w is in meters, speed of paper in meters per second, and frequency f in Hertz.

TABLE 1

| | |
|---|---|
| T = 0.261 | |
| $V_{TOT}$ = 0.856 (g/m²)² | |
| $V_{RES}$ = 0.644 (g/m²)² | RES/TOT % = 75.2 |
| $V_{MD}$ = 0.212 (g/m²)² | MD/TOT % = 24.8 |
| $V_{CMD}$ = 0.081 (g/m²)² | CMD/MD % = 38.2 |
| $V_{NCMD}$ = 0.131 (g/m²)² | NCMD/MD % = 61.8 |

| w(inches) | $COH_{12}$ |
|---|---|
| 17.22 | 0.282 |
| 15.11 | 0.558 |
| 14.95 | 0.487 |
| 12.36 | 0.277 |

TABLE 1-continued

| . | . |
|---|---|
| . | . |
| . | . |
| 6.90 | 0.271 |
| 6.80 | 0.310 |
| 5.74 | 0.821 |
| 5.71 | 0.773 |

$w_{MIN}$ = 3.40 inches
$w_{MAX}$ = 1360.0 inches

The above example demonstrated a preferred embodiment of the invention wherein the analysis was performed with a Fast Fourier Transform Spectrum Analyzer, digital computer and a printer. However, one skilled in the art may perform the analysis by a less preferred analog system. Also, one may prefer to obtain the square root of the variances, wherein the results would be in a more common unit, $g/m^2$ instead of $(g/m^2)^2$.

Furthermore the above analysis may be repeated, whereby fluctuations in the residual variance may be detected over time, such as may be caused by fluctuations in stock consistency or fluctuations in the amount of retention aid added to the pulp.

Having described the invention, modifications will be evident to those skilled in the art without departing from the spirit of the invention, as defined in the appended claims.

I claim:

1. A method for automatically determining on-machine, components of the variance over an entire frequency range (f), of a property of a substantially continuous sheet material comprising:
   (a) allowing said substantially continuous sheet material to travel in a machine direction (MD),
   (b) scanning said sheet material along at least two longitudinally extending locations in a zone across said sheet material and automatically generating an output signal proportional to said property of said sheet material at each of said locations,
   (c) transforming at least two of said output signals into their corresponding power spectral density functions,
   (d) from a pair of said power spectral density functions, determining a coherence function,
   (e) from said coherence function, computing a square root function of said coherence function,
   (f) multiplying said square root function by a first power spectral density function of said pair in step (d), thereby obtaining a machine direction output power, MDOP(f),
   (g) from said machine direction output power, MDOP(f), determining and generating data for the displaying of a machine direction variance over said entire frequency range, $V_{MD}$, by $$V_{MD} = \sum_{i=1}^{n} MDOP(f_i)$$

where MDOP($f_i$) is the machine direction output power at a frequency $f_i$, and n is the number of frequencies in said entire frequency range, with the proviso that said machine direction variance is substantially pure and thereby does not include a residual variance.

2. The method as defined in claim 1, including
   (h) determining a residual variance over said entire frequency range, $V_{RES}$.

3. The method as defined in claim 1 including determining a total variance over said entire frequency range, $V_{TOT}$, by $$V_{TOT} = \sum_{i=1}^{n} G_{FF}(f_i)$$

where $G_{FF}(f_i)$ is said first power spectral density function at a frequency $f_i$, and n is said number of frequencies in said entire frequency range.

4. The method as defined in claim 2 wherein said residual variance over said entire frequency range, $V_{RES}$, is determined by:

$$V_{RES} = \sum_{i=1}^{n} [G_{FF}(f_i) - MDOP(f_i)]$$

where $G_{FF}(f_i)$ is said first power spectral density function at a frequency $f_i$, MDOP($f_i$) is said machine direction output power at a frequency $f_i$, and n is said number of frequencies in said entire frequency range.

5. The method as defined in claim 3 including determining a residual variance over said entire frequency range, $V_{RES}$, by:

$$V_{RES} = V_{TOT} - V_{MD}.$$

6. The method as defined in claim 1 including determining a cyclic machine direction variance over said entire frequency range, $V_{CMD}$, and a non-cyclic machine direction variance over said entire frequency range, $V_{NCMD}$.

7. The method as defined in claim 6 wherein said cyclic machine direction variance over said entire frequency range, $V_{CMD}$, and said non-cyclic machine direction variance over said entire frequency range, $V_{NCMD}$, are determined by:
   computing a threshold value, T, as T=m+(R.s), where m is the mean value of said square root function, R is a factor in the range of 1 to 3.29, and s is the standard deviation of said square root function,
   at each frequency $f_i$ in said entire frequency range, for n number of frequencies, comparing said machine direction output power at said frequency $f_i$, MDOP($f_i$) to said threshold value T, thereby obtaining contributions to said cyclic and non-cyclic machine direction variances over said entire frequency range, $V_{CMD}$ and $V_{NCMD}$ respectively.

8. The method as defined in claim 2 wherein steps b to h are repeated at least once, whereby said sheet material is scanned in at least one different zone across said sheet material, thereby obtaining said residual variance over said entire frequency range, $V_{RES}$, at a plurality of zones across said sheet material.

9. The method as defined in claim 2 wherein steps b to h are substantially simultaneously duplicated in at least one other zone across said sheet material, thereby substantially simultaneously obtaining said residual variance over said entire frequency range, $V_{RES}$, at a plurality of zones across said sheet material.

10. The method as defined in claim 1 wherein said property is chosen from the group comprising basis weight, density, temperature and moisture.

11. An apparatus for automatically determining on-machine, components of the variance over an entire frequency range f, of a property of a substantially continuous sheet material, moving in a machine direction (MD), comprising:
   (a) at least two detectors, each for scanning said sheet material in said machine direction and at a different longitudinally extending location in a zone across said moving sheet material,
   (b) at least two of said detectors each generating a detector output signal proportional to said property of said sheet material at said location,
   (c) means operatively connected to said detectors, for receiving at least two of said detector output signals, converting them and generating converted signals corresponding to their coherence function and at least a first power spectral density functions,
   (d) means, operatively connected to said means for receiving, converting and generating, for receiving and processing said converted signals and generating a processed signal indicative of machine direction variance over said entire frequency range, $V_{MD}$, of the property,
   (e) means, operatively connected to said means for receiving, processing and generating, for receiving and displaying said processed signal indicative of machine direction variance, with the proviso that said machine direction variance is substantially pure and thereby does not include a residual variance.

12. The apparatus as defined in claim 11, (h) wherein said means for receiving, processing and generating further computes a residual variance over said entire frequency range, $V_{RES}$.

13. The apparatus as defined in claim 11 wherein said means for receiving, processing and generating further computes a total variance over said entire frequency range, $V_{TOT}$, whereby $$V_{TOT} = \sum_{i=1}^{n} G_{FF}(f_i)$$

where $G_{FF}(f_i)$ is said first power spectral density function at a frequency $f_i$, and n is said number of frequencies in said entire frequency range.

14. The apparatus as defined in claim 13 wherein said means for receiving, processing and generating further computes a residual variance over said entire frequency range, $V_{RES}$, whereby:

$$V_{RES} = V_{TOT} - V_{MD}.$$

15. The apparatus as defined in claim 11 wherein said means for receiving, processing and generating further computes a cyclic machine direction variance over said entire frequency range, $V_{CMD}$, and a non-cyclic machine direction variance over said entire frequency range, $V_{NCMD}$.

16. The apparatus as defined in claim 11 wherein said detectors are movably mounted.

17. The apparatus as defined in claim 11 wherein said detectors are chosen to detect a property of the group comprising basis weight and moisture, and wherein said sheet material is chosen from the group comprising paper and roofing felt.

18. The apparatus as defined in claim 11 wherein said means for receiving, converting and generating is a spectrum analyzer.

* * * * *